United States Patent [19]

Anderson et al.

[11] Patent Number: 5,114,965
[45] Date of Patent: May 19, 1992

[54] FLUBENZIMINE CONTAINING AGENTS FOR COMBATING PESTS

[75] Inventors: John Anderson, Langenfeld; Bernhard Homeyer, Leverkusen, both of Fed. Rep. of Germany; Walter M. Zeck, Vero Beach, Fla.

[73] Assignees: Bayer Aktiengesellschaft, Leverkusen, Fed. Rep. of Germany; Miles Inc., Pittsburgh, Pa.

[21] Appl. No.: 566,284

[22] Filed: Aug. 13, 1990

Related U.S. Application Data

[62] Division of Ser. No. 938,675, Dec. 5, 1986, Pat. No. 4,965,256.

[30] Foreign Application Priority Data

Dec. 19, 1985 [DE] Fed. Rep. of Germany ....... 3545060

[51] Int. Cl.$^5$ ..................... A01N 43/08; A01N 43/78; A01N 47/10
[52] U.S. Cl. ................................... 514/469; 514/370; 514/477; 514/479; 514/490
[58] Field of Search ............... 514/370, 469, 477, 479, 514/490

[56] References Cited

U.S. PATENT DOCUMENTS

| 2,978,479 | 4/1961 | Kayser et al. | 260/461 |
| 3,621,082 | 11/1971 | Schroder | 260/941 |
| 3,899,584 | 8/1975 | Scholl et al. | 514/370 |
| 4,603,214 | 7/1986 | Anderson et al. | 556/114 |

OTHER PUBLICATIONS

Enhanced Microbial Degradation of Carbofuran and Fensulfothion After Repeated Applications to Acid Mineral Soil-D. C. Read, Agriculture, Ecosystems and Environment 10 (1983) 37–46.

*Primary Examiner*—Allen J. Robinson
*Attorney, Agent, or Firm*—Joseph C. Gil; Lyndanne M. Whalen

[57] ABSTRACT

The foregoing invention relates to new soil pest combating agents which contain at least one conventional active agent, especially a carbamate, P-esters (phosphoric and phosphonic acid esters, including esteramides, as well as corresponding thiono-, thiol- and thiono-thiol derivatives) and pyrethroids as well as Flubenzimin.

5 Claims, No Drawings

FLUBENZIMINE CONTAINING AGENTS FOR COMBATING PESTS

This application is a division of application Ser. No. 938,675, filed Dec. 5, 1986, now U.S. Pat. No. 4,965,256.

FIELD OF THE INVENTION

The present invention relates to new agents for combating pests which can preferably be used in plant protection for combating nematodes and arthropods, in particular insects. The new agents for combating pests comprise at least one nematicidally or arthricidially active compound preferably selected from the group consisting of carbamates, P esters (phosphoric acid esters and phosphonic acid esters, including the ester-amides and the particular thiono, thiol and thiono-thiol derivatives) and pyrethroids combined with Flubenzimine. The new agents for combating pests are distinguished by a particularly long-lasting activity when used as nematicides and soil insecticides.

BACKGROUND OF THE INVENTION

The combating of nematodes and soil insects is gaining ever more importance in intensive cultivation of crop plants. Insects which continuously or at times, for example during certain development stages, live in or on the soil or close to the soil, for example on parts of plants, are designated soil insects (compare also B. Homeyer in Chemie der Pflanzenschutz- und Schädlingsbekämpfungsmittel [Chemistry of the Plant Protection Agents and Agents for Combating Pests], published by R. Wegler, Volume 1, Springer-Verlag, Berlin 1970, pages 464 to 474). Such pests should preferably be combated preventively, so that an agent for combating soil pests must be applied early and must have a reliable and adequate activity for the maximum possible period. It is frequently advantageous for the agents for combating pests already to be applied during sowing, in order to simultaneously achieve protection of the seed and of the developing young plants.

Since the soil treatment agents currently available do not always reliably display an adequately long activity under adverse weather and/or soil conditions, it is an object of the invention to provide new agents for combating pests which allow long-lasting protection of the plants, even under adverse conditions.

SUMMARY OF THE INVENTION

It has now been found that agents for combating pests which contain at least one substance, which is active against nematodes and/or insects, especially soil insects, e.g., carbamates, P esters and pyrethroids, (called the "active compound" below) and Flubenzimine of the formula (I)

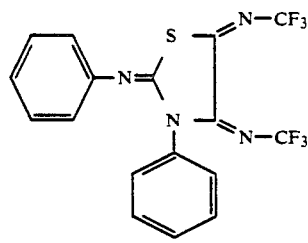

have a particularly long-lasting high activity against nematodes or soil insects. The Flubenzimine of the formula (I) is hereinbelow sometimes identified as "action prolonger" or "extender".

The duration of action of the new pesticidal compositions is considerably longer than the duration of action of the active compounds alone. Since the Flubenzimine of the formula (I) has virtually no nematicidal or soil-insecticidal activity at the concentrations employed, the occurrence of the prolonging of the action must be regarded as decidedly unexpected and surprising.

DETAILED DESCRIPTION OF THE INVENTION

Preferred active compounds for the new agents for combating pests are carbamates, P esters (including the ester-amides and the thiono, thiol and thiono-thiol derivatives) and pyrethroids which are usually employed as agents for combating soil pests (compare Chemistry of Pesticides, edited by K. H. Buchel, John Wiley & Sons, New York, 1983, Farm Chemicals Handbook, Meister Publishing Co., Wolloughby, 1983, U.S. Pat. No. 4,127,652 and European Patent Application 84 105 133.7 and corresponding U.S. patent application Ser. No. 06/606, 106).

The active compounds described below which are preferred are the P esters, carbamates and pyrethroids ($R^1$, $R^2$ and $R^3$ are not used in this text): (A) P esters of the general formula (II)

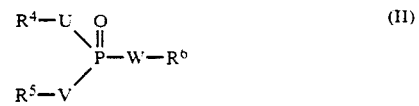

in which

Q represents oxygen or sulphur,

U, V and W are identical or different and represent oxygen or sulphur, it moreover also being possible for one of the radicals U, V and W to denote a direct bond or the -NH- group, $R^4$ and $R^5$ are identical or different and represent $C_1$-$C_4$-alkyl (preferably $C_1$-$C_3$-alkyl) and $R^6$ represents $C_1$-$C_5$-alkyl (preferably $C_1$-$C_2$-alkyl), which can be substituted by $C_1$-$C_4$-alkyl-thio (preferably $C_1$-$C_2$-alkylthio) and/or halogen (preferably chlorine), or represents $C_2$-$C_4$-alkenyl, which can be substituted by halogen (preferably chlorine) and/or halogenophenyl (preferably chlorophenyl) or represents phenyl, which can be substituted by halogen (preferably chlorine and/or bromine), $C_1$-$C_4$-alkyl (preferably methyl), $C_1$-$C_4$-alkylthio (preferably methylthio), $C_1$-$C_4$-alkylsulphinyl (preferably methylsulphinyl) and/or $C_1$-$C_4$-alkoxy-carbonyl (preferably propoxycarbonyl), or represents pyridyl, which can be substituted by halogen (preferably chlorine) or represents pyrimidinyl, which can be substituted by $C_1$-$C_4$-alkyl. $C_3$-$C_6$-cycloalkyl and/or phenyl, or represents the radical 5-chloro-1-(1-methylethyl)-1H-1,2,4- triazol-3-yl, or represents the group -N=CR$^7$ (CN), wherein $R^7$ denotes phenyl which is optionally substituted by halogen (preferably chlorine).

In formula II, $R^4$ and $R^5$ preferably represent methyl, ethyl or n- and i-propyl.

$R^6$ preferably represents chloromethyl, propyl, ethylthiomethyl, ethylthioethyl, t-butylthiomethyl, 1-(2,4-dichlorophenyl))-2-chloro-ethen-1-yl, phenyl, 3-methyl-4-methylthio-phenyl, 4-methylsulphinyl-phenyl, 2-i-propoxy-carbonylphenyl, 2,4-dichlorophenyl, 2,4,5-trichlorophenyl, 2,5-dichloro-4-bromophenyl, 3,5,6-trichloro-2-pyridyl, the radical -N=(CN)(phenyl) or the radical 5-chloro-1-(1-methylethyl)-1-11-1,2,4-triazol-3-yl.

The following P esters may be mentioned as examples (common name or chemical name): disulfoton, femamiphos, isofenfos, trichloronat, fensulfothion, protiofos, phoxim, chlorfenvinfos, bromophos, terbufos, chlorpyrifos, chlormephos, fenofos, isazophos, ethoprofos, phorate, O-ethyl O-i-propyl O-(2-t-butyl-pyrimidin-5-yl) thionophosphate and O,O-diethyl O-(2-t-butyl-pyrimidin-5-yl) thionophosphate. Preferred esters which may be mentioned are: terbufos, chlorpyrifos, fenafos, isofenfos, fenaminphos, phorate, O-ethyl O-i-propyl O-(2-t-butyl-pyrimidin-5-yl) thionophosphate and O,O-diethyl 0-(2-t-butyl-pyrimidin-5-yl) thionophosphate.

(B) Carbamates of the general formula (III)

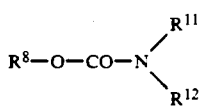 (III)

in which $R^8$ represents phenyl, which can be substituted by $C_1$-$C_4$-alkylthio-$C_1$-$C_4$-alkyl (preferably ethylthiomethyl) $C_1$-$C_4$-alkyl (preferably methyl), $C_1$-$C_4$-alkoxy and/or $C_1$-$C_4$-alkylthio (preferably methylthio), or represents the radical 2,3-dihydro-2,2-dimethyl-7-benzofuranyl, or represents the radical -N=$CR^9R^{10}$, in which $R^9$ denotes $C_1$-$C_4$-alkyl (preferably propyl), which can be substituted by $C_1$-$C_4$-alkylthio (preferably methylthio), or $R^9$ denotes the radical CON ($C_1$-$C_4$-alkyl)$_2$ preferably CON(CH$_3$)$_2$) and $R^{10}$ denotes hydrogen or $C_1$-$C_4$-alkylthio (preferably methylthio), $R^{11}$ represents $C_1$-$C_4$-alkyl (preferably methyl) and $R^{12}$ denotes hydrogen or the radical -S-$NR^{13}R^{14}$, in which $R^{13}$ denotes $C_1$-$C_4$-alkyl and $R^{14}$ denotes $COOC_1$-$C_4$-alkyl (preferably n-butyl) or $C_1$-$C_4$-alkyl, which can be substituted by $COO$-$C_1$-$C_4$-alkyl (preferably $COOC_2H_5$), $R^8$ preferably represents 3,4,5-trimethylphenyl, 2-ethylthiomethylphenyl, 3,5-dimethyl-4-methylthophenyl, 2,3-dihydro-2,2-dimethyl-7-benzofuranyl, -N=CHC(CH$_3$)$_2$(SCH$_3$), -N=C(SCH$_3$)(CON(CH$_3$)$_2$) or 2-i-propoxyphenyl, $R^{11}$ preferably represents methyl, $R^{12}$ preferably represents hydrogen, -S-N(CH$_3$)(COOC$_4$H$_9$n), -S-N(C$_4$H$_9$n)$_2$ or -S-N(iC$_3$H$_7$)(CH$_2$CH$_2$COOC$_2$H$_5$).

The following carbamates may be mentioned as examples (common name or chemical name): ethiofencarb, carbofuran, methiocarb, furatiocarb, carbosulfan, inosulfuram, aldicarb, oxamyl and 3,4,5-trimethylphenyl carbamate. Carbamates which may be mentioned as preferred are: carbofuran, furatiocarb, carbosulfan, aminosulfuram and aldicarb.

(C) Pyrethroids of the general formula (IV)

 (IV)

in which
$R^{15}$ represents the group

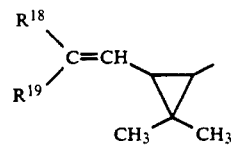

in which
$R^{18}$ denotes halogen (preferably chlorine or bromine) or $C_1$-$C_4$-alkyl (preferably methyl) and
$R^{19}$ denotes halogen (preferably chlorine or bromine) $C_1$-$C_4$-alkyl (preferably methyl) or phenyl, which can be substituted by halogen (preferably chlorine), or
$R^{15}$ represents the group

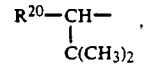

in which
$R^{20}$ denotes phenyl, which can be substituted by halogen (preferably chlorine), $C_1$-$C_4$-halogenoalkyl (halogen is preferably chlorine or fluorine), $C_1$-$C_4$-halogenoalkoxy (halogen is preferably chlorine or fluorine) and/or $C_1$-$C_4$-alkoxy,
$R^{16}$ represents hydrogen or cyano and
$R^{17}$ represents phenyl, which can be substituted by halogen (preferably fluorine or chlorine) and/or phenoxy.

$R^{18}$ and $R^{19}$ in the groups $R^{15}$ preferably represent chlorine, bromine or methyl, or $R^{18}$ represents chlorine and $R^{19}$ represents 4-chlorophenyl. $R^{20}$ preferably represents 4-chlorophenyl or 2-chloro-4-trifluoromethylphenyl.

17 preferably represents pentafluorophenyl, 3-phenoxyphenyl or 4-fluoro-3-phenoxyphenyl.

Examples of pyrethroids which may be mentioned are (common name): phenothrin, permethrin, decamethrin, fenvalerat, fluvalinate, cyfluthrine and fenfluthrin.

The present invention thus relates to a new use of the Flubenzimine of the formula (I) as an agent for prolonging the action of nematicidal and insecticidal carbamates, P esters and pyrethroids, agents for combating soil pests containing the compound of the formula (I) and at least one nematicidal or insecticidal active compound from the series of insecticidal active compounds comprising the carbamates P esters and pyrethroids, and the use of these agents for combating pests for combating soil pests, preferably nematodes and insects. For simplicity, the term insects will in each case also include the less important arthropods which occur as soil pests, for example ants, springtails, millepedes, termites woodlice and root mites.

Flubenzimine of formula (I) is a known compound (c.f. German Patent No. 2,062,348 or U.S. Pat. Nos. 3,895,020 and 3,899,584).

The new mixtures of the active compounds and the extender can be employed against a large number of nematodes and insects, typical soil pests being the focus, but it also being possible to affect all the other important arthropods which usually occur, or occur only purely accidentally at times, in the soil or close to the soil.

From the order of the Isopoda, for example, *Oniscus asellus, Armadillidium vulgare* and *Porcellio scaber*. From the order of the Diplopoda, for example, *Blaniulus guttulatus*. From the order of the Chilopoda, for example, *Geophilus carpophagus* and Scutigera spec. From the order of the Symphyla, for example, *Scutigerella immaculata*. From the order of the Thysanura, for example, *Lepisma saccharina*. From the order of the Collembola, for example, *Onychiurus armatus*. From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria*. From the order of the Dermaptera, for example, *Forficula auricularia*. From the order of the Isoptera, for example, Reticulitermes spp. From the order of the Anoplura, for example, *Phylloxera vastatrix, Pemphigus spp., Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci*. From the order of the Heteroptera, for example, Eurygaster spp., *Dysdercus intermedius, Piesma quadrate, Cimex lectularius, Rhodnius prolixus* and Triatoma spp. From the order of the Homoptera, for example, *Aleurodes brassicae, B. aisia tabaci, Trialeurodes vaporariorum, Aphis gossypii, Brevicoryne brassicae, Cryptomyzus ribis, Doralis fabae, Doralis pomi, Erisoma Lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvate Lugens, Aonidiella aurantii, Aspidiotus hederae,* Pseudococcus spp. and Psylla spp. From the order of the Ledidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrostis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudopretella, Cacoecia podana, Capus reticulana, Choristoneura fumiferana, Clysis ambiguella, Homona magnanima* and *Tortrix viridana*. From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineta, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica*. From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa*. From the order of the Siphonaptera, for example, *Xenopsylia cheopis* and Ceratophyllus spp.

The phytoparasitic nematodes include, for example, Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp. and Trichodorus spp.

The new agents for combating pests are particularly preferably employed against the above mentioned nematodes. Moreover, they are preferably employed against pests from the group of the "corn rootworms" of the genera Diabrotica, such as *Diabrotica virgifera, Diabrotica balteata* and *Diabrotica longicornis*.

The mixtures of active compounds and extenders can be converted to the customary formulations, such as solutions, emulsions, suspensions, powders, granules, natural and synthetic materials impregnated with active compound and very fine capsules in polymeric substances and in coating compositions for seed.

These formulations are produced in known manner, for example by mixing the active compounds with diluents, that is, liquid solvents and/or solid carriers, optionally with the use of surface-active agents, that is, emulsifying agents and/or dispersing agents, and/or foam-forming agents. In the case of the use of water as a diluent, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetones, methyl ethyl ketone, methyl isobutyl ketone or cyclohexanone, strongly polar solvents, such as dimethylformamide and dimethylsulphoxide, as well as water.

As solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates: as solid carriers for granules there are suitable: for example crushed and fractionated natural rocks, such as calcite, marble, pumice, sepiolite, dolomite and brick gravel, as well as synthetic granules of inorganic and organic meals, and granules of organic material such as sawdust, coconut shells, corn cobs and tobacco stalks: as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumen hydrolysis products: as dispersing agents there are suitable: for example lignin-sulphite waste liquors and methylcellulose.

Adhesives such as carboxymethylcellulose and natural and synthetic polymers in the form of powders, granules or lattices, such as gum arabic, polyvinyl alcohol and polyvinyl acetate, as well as natural phospholipids, such as cephatins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Preferred formulation forms are granules, emulsifiable concentrates, suspension concentrates and water-dispersible powders, particularly preferred are granules.

The formulations in general contain between 0.1 and 95 percent by weight of the mixture of active compound and extender, preferably between 0.5 and 90%.

It is also possible to formulate the active compounds and extenders separately and to mix the formulated products, or to apply the formulated products separately in their formulations.

The mixtures according to the invention can be present in their commercially available formulations and in the use forms, prepared from these formulations, as well as in a mixture with other active compounds, such as other insecticides, baits, sterilizing agents, acaricides, nematicides, fungicides or growth-regulating substances. The other insecticides, include, for example, phosphates, carbamates, carboxylates, chlorinated hydrocarbons, phenylureas, pyrethroids, substances produced by microorganisms, and others.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The mixtures are employed in a customary manner appropriate for the use forms. As already indicated above, it is also possible to use the active compounds and extenders in (optionally different) separate formulations in mixtures of the formulations or as separate formulations.

The active compound content of the use forms prepared from the commercially available formulations can vary within wide limits. The active compound concentration of the use forms can be from 0.0000001 to 95% by weight of active compound, preferably between 0.0001 and 20% by weight.

The proportions of active compound to extender in the formulations can vary within wide limits, depending on the chosen extender and the relative activity of the particular active compound used and the active compound content in the formulation, without the prolonging in action being lost. The ratios (weight ratios) of active compounds/extender are preferably between the ranges of 1:50 and 50:1, particularly preferably between 1:20 and 20:1 and very particularly preferably between 1:10 and 10:1.

The new mixtures of active compounds and extenders are preferably employed in amounts of between 0.1 and 10 kg/ha, preferably between 0.5 and 5 kg/ha, and particularly preferably between 0.8 and 2 kg/ha (based on the non-formulated substances).

The expert can easily determine the most advantageous formulations, compositions and use amounts for solving the particular problems with the aid of his expert knowledge or with the aid of simple orientating experiments.

The prolonged duration of action of the new mixtures according to the invention may be illustrated by the following examples.

In order rapidly to achieve advantageous results in the discovery and development of suitable extenders under laboratory and greenhouse conditions, model soils suitable for the investigations were developed and the tests were carried out at relatively high soil temperatures of 20°-25° C.

The particularly preferred active compounds employed in Examples A and B can be illustrated by the following formulae:

1. Carbofuran:

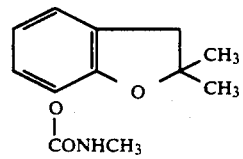

2. Isofenphos

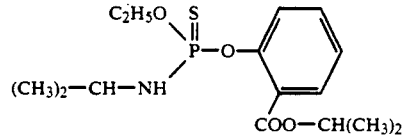

3. Fenamiphos

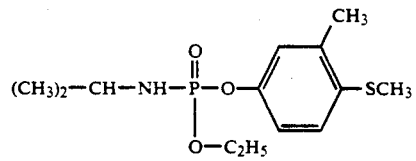

EXAMPLE A

1. Model soil used
Composition (percent by weight):
60% of garden soil
30% of sand
10% of peat 2. Experimental Procedure and results For the investigations, in each case 4 mg of active compound by itself or a mixture of in each case 4 mg of active compound and 4 mg of the flubenzimin extender were mixed with in each case 1 l of the model soil, so that the individual substances were in each case present in concentrations of 4 ppm. After storage of the soils thus pretreated, after 1 week ½ l of soil and after 4 weeks the remaining half l were infested with 20 seven day-old larvae of Diabrotica balteata. On the day of infestation pre-swollen corn seeds were placed on the bottom of each container so that, upon germination into seedlings, they served as food for the larvae.

In each case 6 days after the infestation with the test larvae, the degree of action of the active compound by itself and of the mixture of active compound and extender were determined in % by counting the dead and living larvae. The degree of action is 100% if all the test larvae have been destroyed, and is 0% if just as many test larvae survive as in the case of the untreated control.

The active compound, amounts applied and results can be seen from the following tables:

EXAMPLE A1

Active compound: Carbofuran

| Active Compound Concentration in ppm | Extender Concentration in ppm | % Destruction of the Diabrotica larvae After | |
|---|---|---|---|
| | | 1 week | 4 weeks |
| 5 | 0 | 100 | 0 |
| 0 | 5 | 0 | 0 |
| 5 | 5 | 100 | 100 |

EXAMPLE A2

Active compound: Isohpenphos

| Active compound Concentration in ppm | Extender Concentration in ppm | % Destruction of the Diabrotica larvae | |
|---|---|---|---|
| | | 1 week | 4 weeks |
| 5 | 0 | 100 | 0 |
| 0 | 5 | 0 | 0 |
| 5 | 5 | 100 | 100 |

The extender by itself had no destructive action in the concentrations used.

The foregoing experiments, which involved illustrative concentrations, show that the mixtures of active compounds and the extender exhibit high activity significantly longer than the active compounds themselves.

EXAMPLE B

Model soil and test procedure correspond to Example A. However, Musca domestica larvae were used as test larvae. Fenamiphos was used as active ingredient (active compound 3).

| Active compound Concentration in ppm | Extender Concentration in ppm | % Destruction of the Musca larvae after | |
|---|---|---|---|
| | | weeks | weeks |
| 5 | 0 | 100 | 0 |
| 0 | 5 | 0 | 0 |
| 5 | 5 | 100 | 100 |

It will be understood that the specification and examples are illustrative but not limitative of the present invention and that other embodiments within the spirit and scope of the invention will suggest themselves to those skilled in the art.

What is claimed is:

1. A pesticidal composition for soil application displaying an enhanced duration of activity comprising an effective amount of a carbamate soil pesticide and an effective amount for enhancing the period of activity of said pesticide, flubenzimine wherein the weight ratio of soil pesticide to flubenzimine is between about 1:50 and 50:1.

2. The composition of claim 1 in which the pesticide is carbofuran.

3. A process for combating nematodes and soil insects comprising the application of an insecticidally or nematicidally effective amount of the composition of claim 1 to soil which is the site of an actual or potential infestation.

4. The process of claim 3 wherein
   a) an insecticidally effective amount of the composition of claim 1 is applied,
   b) the weight ratio of the flubenzimine to the soil pesticide is between about 1:50 and 50:1, and
   c) the mixture is applied at a rate between about 0.1 and 10 kilograms per hectare.

5. The process of claim 4 wherein the soil pesticide is carbofuran.

* * * * *